(12) United States Patent
Hjorth et al.

(10) Patent No.: US 8,053,626 B2
(45) Date of Patent: Nov. 8, 2011

(54) ABSORBENT ARTICLE CONTAINING A SKINCARE COMPOSITION AND METHOD OF MAKING AND USING SAME

(75) Inventors: Madeleine Hjorth, Gothenburg (SE); Anne Farbrot, Askim (SE); Bo Runeman, Partille (SE); Christine Wild, Hilden (DE); Raymond Mathis, Dusseldorf (DE); Michael Neuss, Cologne (DE)

(73) Assignee: SCA Hygiene Products AB, Gothenburg (SE)

( * ) Notice: Subject to any disclaimer, the term of this patent is extended or adjusted under 35 U.S.C. 154(b) by 1885 days.

(21) Appl. No.: 10/458,651

(22) Filed: Jun. 11, 2003

(65) Prior Publication Data

US 2004/0024374 A1 Feb. 5, 2004

Related U.S. Application Data

(60) Provisional application No. 60/387,593, filed on Jun. 12, 2002.

(51) Int. Cl.
*A61F 13/15* (2006.01)
*A61F 13/20* (2006.01)
*A61F 13/00* (2006.01)
*A01N 25/34* (2006.01)
*A61K 9/70* (2006.01)
*A61M 35/00* (2006.01)

(52) U.S. Cl. ........ 604/364; 604/358; 604/289; 424/402; 424/443; 424/404

(58) Field of Classification Search .......... 604/289, 604/304, 308, 367, 375, 385.01; 602/48, 602/51; 424/402

See application file for complete search history.

(56) References Cited

U.S. PATENT DOCUMENTS

| | | | | |
|---|---|---|---|---|
| 3,896,807 A | * | 7/1975 | Buchalter | 604/289 |
| 4,895,567 A | * | 1/1990 | Colon et al. | 604/361 |
| 5,389,374 A | * | 2/1995 | Brown-Skrobot | 424/431 |
| 5,660,842 A | * | 8/1997 | Petschow | 424/405 |
| 5,968,025 A | * | 10/1999 | Roe et al. | 604/364 |
| 6,063,397 A | * | 5/2000 | Fowler et al. | 424/443 |
| 6,120,783 A | * | 9/2000 | Roe et al. | 424/402 |
| 6,156,024 A | | 12/2000 | Schulte et al. | |
| 6,749,860 B2 | * | 6/2004 | Tyrrell et al. | 424/404 |
| 2002/0055562 A1 | * | 5/2002 | Butuc | 524/80 |
| 2002/0058916 A1 | * | 5/2002 | Hisanaka et al. | 604/360 |

FOREIGN PATENT DOCUMENTS

DE 33 09 530 10/1984

(Continued)

OTHER PUBLICATIONS

Office Action issued in corresponding Mexican Patent Application dated Mar. 13, 2009 with partial English translation.

(Continued)

*Primary Examiner* — Tatyana Zalukaeva
*Assistant Examiner* — Susan Su
(74) *Attorney, Agent, or Firm* — Buchanan Ingersoll & Rooney PC

(57) ABSTRACT

An absorbent article has a skincare composition applied on at least a portion thereof so as to be transferable to the skin of the wearer. The composition is solid at 21° C. and includes at least three constituents, being chosen according to their melting behavior, and characterized, in particular, by the presence of a crystallization accelerator.

62 Claims, 1 Drawing Sheet

FOREIGN PATENT DOCUMENTS

| | | |
|---|---|---|
| EP | 1035818 | 4/2002 |
| EP | 1192955 A2 | 4/2002 |
| JP | 11-510082 | 9/1999 |
| JP | 2000-505682 | 5/2000 |
| JP | 2001-19634 | 1/2001 |
| JP | 2001-515022 | 9/2001 |
| JP | 2001-314440 | 11/2001 |
| JP | 2001-522697 | 11/2001 |
| JP | 2002-541982 | 12/2002 |
| WO | WO 96/16682 | 6/1996 |
| WO | WO 99/27876 | 6/1999 |
| WO | WO 00/64502 | 11/2000 |
| WO | WO 00/71177 | 11/2000 |
| WO | WO 01/00129 | 1/2001 |
| WO | WO 01/22933 | 4/2001 |
| WO | WO 01/35883 A1 * | 5/2001 |
| WO | WO 02/051456 | 7/2002 |

OTHER PUBLICATIONS

Notice of Reasons for Rejection issued in corresponding Japanese Patent Application No. 2004-512816, mailed Jul. 18, 2008, and translation thereof.

Summary of Office Action issued on Jun. 26, 2008 in a corresponding patent application pending in Columbia.

Communication of Notice of Opposition dated Dec. 30, 2009 issued in the corresponding European Patent No. EP 1371379.

Nick Vega, Experimental Report, Cooling Characteristic Test, Oct. 30, 2009, pp. 1-2.

* cited by examiner

ABSORBENT ARTICLE CONTAINING A SKINCARE COMPOSITION AND METHOD OF MAKING AND USING SAME

CROSS-REFERENCE TO RELATED APPLICATION

This application claims priority to U.S. Provisional Application No. 60/387,593, filed Jun. 12, 2002, entitled "Absorbent Article Containing a Skincare Composition," hereby incorporated by reference and relied upon in its entirety for all purposes.

TECHNICAL FIELD

The present invention relates to an absorbent article such as a diaper, pant diaper, incontinence pad, sanitary napkin, pantiliner, and the like. In particular, the present invention relates to absorbent articles having a skincare composition applied on at least a portion thereof, with the composition being transferable to the skin of the wearer by normal contact and wearer motion and/or body heat.

BACKGROUND OF THE INVENTION

In the preparation of hygiene articles, such as baby diapers or sanitary towels, absorbing materials are used in order to absorb aqueous fluids. In order to prevent direct contact with the absorbing material upon wearing and to increase the wear comfort, this material is covered with a thin, water-pervious nonwoven. Nonwoven materials of this type are usually prepared from synthetic fibers, such as polyolefin or polyester fibers, because these fibers can be produced at low cost, have good mechanical properties, and are thermally stable.

In the hygiene article sector, nonwoven materials of this type are increasingly provided with skin-friendly lotions in order to generally improve tolerability and wear comfort. For example, DE 33 09 530 C1 describes a hygienic absorption liner impregnated with a skincare material which consists of triglycerides and/or partial glycerides of coconut oil fatty acids having 8 to 18 carbon atoms. In order that these preparations can transfer from the nonwoven to the skin without problems while being worn, the triglyceride and partial glyceride mixtures of DE 33 09 530 are chosen such that they have a rise point in the range from 35° C. to 40° C.

Another approach to transferring skincare substances to the skin during the wearing of hygiene articles is given in WO 96/16682. This describes a diaper whose inner covering web is prepared with a lotion which is solid or semisolid at 20° C. and which transfers to the skin of the wearer while being worn. These lotions comprise from 10% to 95% of an anhydrous emollient, which has to be plastic or liquid at room temperature, and 5% to 90% of a so-called immobilizer which is to have a melting point of at least 35° C., but preferably 40° C.

However, the main problem of the known lotions is their storage stability. It is preferable that the lotions themselves are in a form at skin temperature, i.e., approximately 36° C. to 38° C., such that they transfer to the skin from the nonwoven without difficulty, i.e., at these temperatures the lotion should be sufficiently viscous to detach from the nonwoven and transfer onto the skin. This temperature-dependent process can, however, lead to problems if the hygiene products are stored at relatively high temperatures, e.g., more than 30° C. In this case, it is frequently observed that the lotions "exude" on the nonwoven materials. It was therefore an object of the present invention to provide skin-friendly lotions for application to nonwoven materials for hygiene articles, where the storage stability of said lotions is to be ensured, in particular at high temperatures.

Furthermore, it is to be noted that the nonwoven in, e.g., baby diapers must be pervious to liquids and has therefore usually been prepared to be hydrophilic. Further finishing with a usually hydrophobic skin-friendly lotion could therefore reduce or significantly impair the transportation of liquid through the web into the absorbing materials.

Furthermore, it is desired that the lotions transfer as completely as possible from the nonwoven onto the skin of the wearer and, in this connection, optionally provide further additional uses, e.g., the reduction of odor formation or the growth of bacteria, fungi, and yeasts. In principle, it should be possible to apply the lotions to the nonwoven materials easily and to apply them as far as possible using the known preparation processes. It has been found that these properties could not be achieved in totality using the products of the prior art.

The lotion composition is typically applied to the absorbent article or a material intended to be used in such an article, in a molten state. This is normally done at a temperature between 35° C. and 100° C. Once the molten lotion has been applied it is allowed to cool and solidify to form solidified coating on the surface of the article or material onto which it has been applied. Any suitable application methods such as slot coating, extrusion coating, gravure coating, and spraying methods may be used.

One main problem when applying lotion compositions to absorbent articles or a material intended to be used in such articles is that the manufacturing process often is a very rapid process and the molten lotion will not solidify sufficiently before the article or material is folded or rolled up, resulting in smearing of the lotion. The lotion may further penetrate through, e.g., the topsheet of the absorbent article, onto which it has been applied, and migrate into the absorbent core making this hydrophobic and less absorbent.

SUMMARY

It is an object of the present invention to provide an absorbent article containing a lotion of the above mentioned kind and which overcome or at least reduce the problems of smearing during the manufacturing of the article and penetration through the material onto which the lotion has been applied. Surprisingly, it has been found that by combining three components chosen on the basis of their melting behavior, it is possible to achieve the above object.

The present invention thus provides, in a first embodiment, an absorbent article such as a diaper, pant diaper, adult incontinence guard, sanitary napkin and the like comprising a liquid permeable topsheet, a liquid impermeable backsheet and an absorbent body enclosed therebetween, said article having a skin treating composition applied on at least a portion thereof so as to be transferable to the skin of the wearer, the composition being solid at 21° C. and comprising the following components:

a) 5% to 70% by weight of a component melting in the range from 25° C. to 37° C., chosen from the group of synthetic waxes, paraffins, fatty acid esters, polyhydroxy fatty acid esters, fatty alcohols, alkoxylated fatty acid esters, alkoxylated fatty alcohols and mixtures of these compounds;

b) 5% to 70% by weight of a component whose melting point is at least 5° C. higher than the melting point of component a), and component b) is chosen from the group of paraffins, polyhydroxy fatty acid esters, $C_{14}$-$C_{22}$ fatty alcohols, $C_{12}$-$C_{22}$ fatty acids, the alkoxylated derivatives of the fatty alcohols and fatty esters, and mixtures of these components;

c) 5% to 25% by weight of a crystallization accelerator chosen from the group of partial glycerides, ethylene glycol diesters and polymeric waxes, with the proviso that the crystallization accelerator has a melting point in the range from 45 to 70° C., and the composition comprises less than 5% by weight of water.

The compositions according to embodiments of the invention comprise three constituents, being characterized, in particular, by the presence of component c), a crystallization accelerator. Furthermore, it is desirable to chose components a) to c) according to their melting behavior.

In a preferred embodiment, component b) has a melting point in the range from 40 to 60° C.

In one embodiment of the invention, component a) is chosen from the mixtures of glycerides of fatty acids having 8 to 18 carbon atoms, preferably from technical-grade mixtures of partial glycerides and/or mixtures with glycerides.

In another embodiment of the invention, component b) is chosen from mixtures of glycerides of fatty acids having 8 to 18 carbon atoms, preferably from technical-grade mixtures of partial glycerides and/or mixtures with glycerides.

Components a) and/or b) may each comprise glycerol triesters or partial esters of coconut fatty acids, the mixtures in each case having a melting point in the claimed range.

Component c) is comprises glycerol partial esters with $C_{12}$-$C_{21}$ fatty acids, preferably glycerol monolaurate, in one embodiment.

In still another embodiment, component c) is a polyvinyl stearyl ether.

Preferably, the skincare composition comprises component a) in amounts of from 10% to 60% by weight, component b) in amounts of from 10% to 60% by weight and component c) in amounts of from 10% to 25% by weight.

In other embodiments, it is further preferred that the skincare composition has a melting point in the range from 35° C. to 65° C., preferably from 35° C. to 50° C., and in particular, from 35° C. to 45° C.

In another embodiment, the skincare composition may further comprise silicone waxes in amounts of from 1% to 6% by weight, preferably 1.5% to 5.5% by weight and in particular from 2% to 5% by weight.

In other embodiments of the skincare composition may further comprise skin-friendly and/or skincare substances in amounts of from 0.1% to 10% by weight, preferably 1% to 8% by weight and in particular, from 2% to 6% by weight.

In one embodiment of the invention the skincare composition comprises water in amounts of from 0.5% to 3% by weight, preferably 0.5% to 2% by weight, and in particular, 0.5% to 1.5% by weight.

In one embodiment, the skincare composition comprises 50% to 60% by weight of a mixture of glycerol esters of coconut fatty acids having a melting point of from 30° C. to 33° C. as component a), 10% to 20% by weight of a linear, unsaturated fatty alcohol having a melting point of from 57° C. to 60° C. as component b), 15% to 20% of polyvinyl stearyl ether having a melting point of from 45° C. to 48° C. as component c), and, optionally, 2% to 5% by weight of silicone wax and 5% to 10% by weight of a skincare substance.

Another object of the invention provides for a method of applying a skin care composition comprising applying an absorbent article to the skin of a wearer wherein the absorbent article comprises a liquid permeable topsheet, a liquid impermeable backsheet, an absorbent body enclosed therebetween, and a skincare composition applied on at least a portion of the absorbent article so as to be transferable to the skin of a wearer, wherein the skincare composition is solid at 21° C. and comprises the following components:

a) 5% to 70% by weight of a component melting in the range from 25° C. to 37° C. selected from the group consisting of synthetic waxes, paraffins, fatty acid esters, polyhydroxy fatty acid esters, fatty alcohols, alkoxylated fatty acid esters, alkoxylated fatty alcohols, and mixtures thereof;

b) 5% to 70% by weight of a component whose melting point is at least 5° C. higher than the melting point of component a) wherein component b) is selected from the group consisting of paraffins, polyhydroxy fatty acid esters, $C_{14}$-$C_{22}$ fatty alcohols, $C_{12}$-$C_{22}$ fatty acids, alkoxylated fatty alcohols and fatty esters, and mixtures thereof; and c) 5% to 25% by weight of a crystallization accelerator selected from the group consisting of partial glycerides, ethylene glycol diesters, and polymeric waxes, with the proviso that the crystallization accelerator has a melting point in the range from 45 to 70° C.

In one embodiment, the skincare composition comprises less than 5% by weight of water.

Another object of the invention is to provide a method of making an absorbent article with a skincare composition comprising applying a skincare composition to an absorbent article or a material to be incorporated into an absorbent article, wherein the skincare composition is solid at 21° C. and comprises the following components:

a) 5% to 70% by weight of a component melting in the range from 25° C. to 37° C. selected from the group consisting of synthetic waxes, paraffins, fatty acid esters, polyhydroxy fatty acid esters, fatty alcohols, alkoxylated fatty acid esters, alkoxylated fatty alcohols, and mixtures thereof;

b) 5% to 70% by weight of a component whose melting point is at least 5° C. higher than the melting point of component a) wherein component b) is selected from the group consisting of paraffins, polyhydroxy fatty acid esters, $C_{14}$-$C_{22}$ fatty alcohols, $C_{12}$-$C_{22}$ fatty acids, alkoxylated fatty alcohols and fatty esters, and mixtures thereof; and c) 5% to 25% by weight of a crystallization accelerator selected from the group consisting of partial glycerides, ethylene glycol diesters, and polymeric waxes, with the proviso that the crystallization accelerator has a melting point in the range from 45 to 70° C.

In one embodiment, the skincare composition comprises less than 5% by weight of water.

In one embodiment, the skincare composition is applied on at least part of the topsheet of the absorbent article. Different amounts of skincare composition may be applied in different zones of the topsheet. For example, the intended wetting region of the topsheet material may contain no or a smaller amount of skincare composition as compared to the surrounding regions of the topsheet material.

In still a further embodiment, the skincare composition is applied on any material and component of the article, such as elastic members, belts, fibers, etc., which is in contact with the skin of the wearer during use of the article via, e.g., the liquid pervious topsheet.

In a further embodiment of the invention, at least two different skincare compositions are applied in different regions of the article.

DETAILED DESCRIPTION OF THE PREFERRED EMBODIMENTS

The term "absorbent article" refers to products that are placed against the skin of the wearer to absorb and contain body exudates, like urine, feces and menstrual fluid. The invention mainly refers to disposable absorbent articles, which means articles that are not intended to be laundered or otherwise restored or reused as an absorbent article after use. Examples of disposable absorbent articles include feminine hygiene products such as sanitary napkins, pantiliners, and sanitary panties; diapers and pant diapers for infants and incontinent adults; incontinence pads; diaper inserts and the like.

Figure 1:
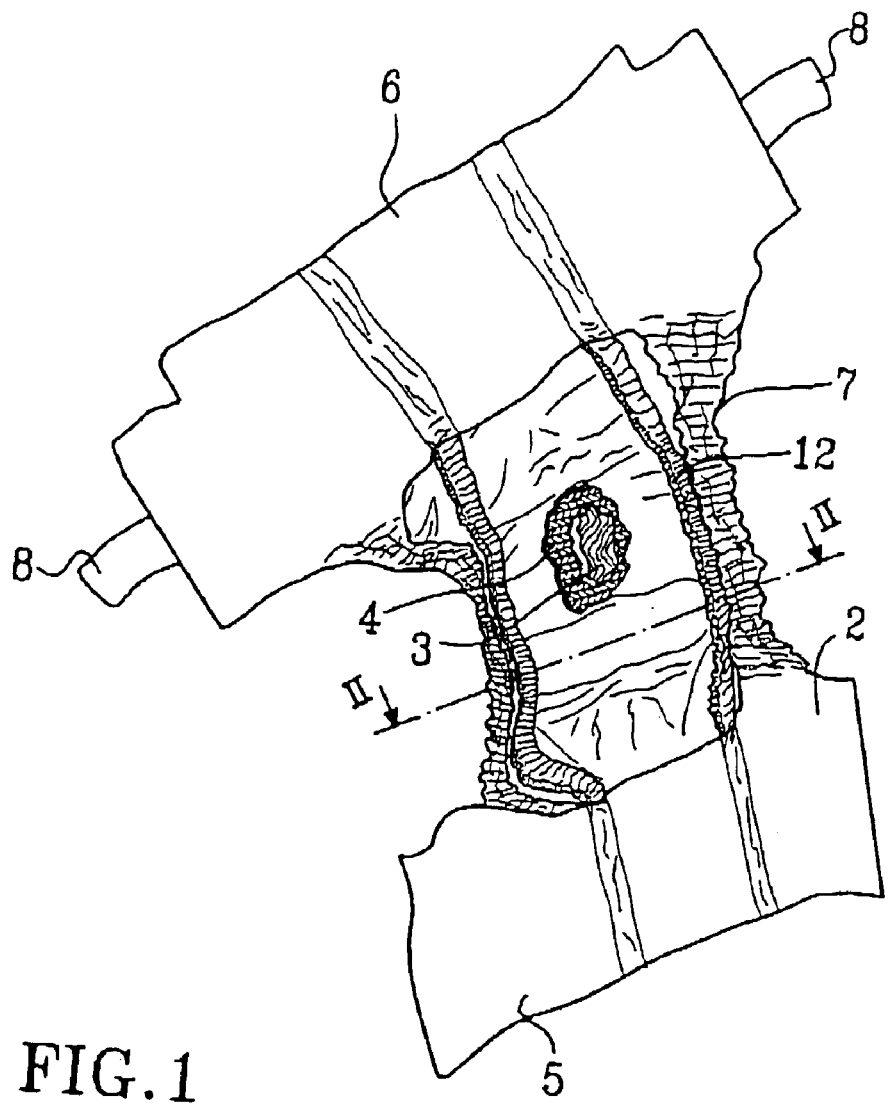
FIG. 1 is a perspective view of an absorbent article in the form of a diaper.

FIG. 1 an embodiment of a diaper 1 for an infant or an incontinent adult, said diaper typically comprises a chassis comprising a liquid permeable topsheet 2, a liquid impermeable backsheet 3 and an absorbent body 4 enclosed therebetween. The liquid permeable topsheet 2 can consist of a non-woven material, e.g., spunbonded, meltblown, carded, hydroentangled, wetlaid, etc. Suitable nonwoven materials can be composed of natural fibers, such as woodpulp or cotton fibers, manmade fibers, such as polyester, polyethylene, polypropylene, viscose, etc., or a mixture of natural and man-made fibers. The topsheet material may further be composed of tow fibres, which may be bonded to each other in a bonding pattern, as, e.g., disclosed in EP-A-1 035 818. Further examples of topsheet materials are porous foams, apertured plastic films, etc. The materials suited as topsheet materials should be soft and non-irritating to the skin and be readily penetrated by body fluid, e.g., urine or menstrual fluid.

The liquid impermeable backsheet 3 may consist of a thin plastic film, e.g., a polyethylene or polypropylene film, a nonwoven material coated with a liquid impervious material, a hydrophobic nonwoven material that resists liquid penetration, or laminates of plastic films and nonwoven materials. The backsheet material may be breathable so as to allow vapor to escape from the absorbent core, while still preventing liquids from passing through the backsheet material.

The topsheet 2 and the backsheet material 3 have a somewhat greater extension in the plane than the absorbent body 4 and extend outside the edges thereof. The layers 2 and 3 are connected to each other within the projecting portions thereof, e.g., by gluing or welding by heat or ultrasonic. The topsheet and/or the backsheet may further be attached to the absorbent core by any method known in the art, such as adhesive, heatbonding, etc. The absorbent core may also be unattached to the topsheet and/or the backsheet.

The absorbent body 4 can be of any conventional kind. Examples of commonly occurring absorbent materials are cellulosic fluff pulp, tissue layers, highly absorbent polymers (so called superabsorbents), absorbent foam materials, absorbent nonwoven materials, or the like. It is common to combine cellulosic fluff pulp with superabsorbents in an absorbent body. It is also common to have absorbent bodies comprising layers of different material with different properties with respect to liquid acquisition capacity, liquid distribution capacity and storage capacity. This is well-known to the person skilled in the art and therefore does not have to be described in detail. The thin absorbent bodies, which are common in, e.g., baby diapers and incontinence guards, often comprise a compressed mixed or layered structure of cellulosic fluff pulp and superabsorbent. The size and absorbent capacity of the absorbent core may be varied to be suited for different uses such as baby diapers, adult incontinence diapers and pads, pant diapers, pantiliners, sanitary napkins etc.

The diaper embodiment disclosed in FIG. 1 is intended to enclose the lower part of the wearer's trunk like a pair of absorbent pants. It comprises a front portion 5 intended during use to be worn on the front part of the user's body, a rear portion 6 intended during use to be worn on the rear part of the user's body, and a more narrow crotch portion 7 located between the front and rear portions and which is intended to be worn in the crotch part of the user between the legs. The front portion 5 is provided with a pair of adhesive tape tabs 8 or other type of attachment means such as hook-and-loop type fasteners.

Figure 2:
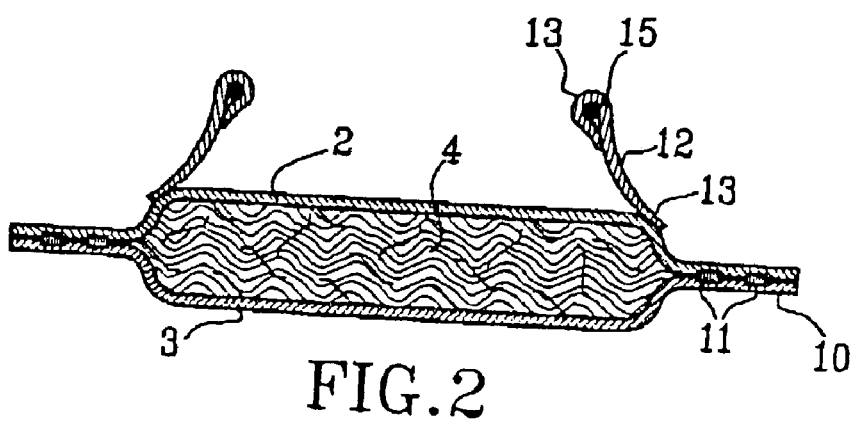
FIG. 2 is a fragmentary sectional view through an absorbent article.

In one embodiment, the diaper comprises elasticized side flaps 10 forming leg openings. Elastification is provided by elastic members 11 secured between the topsheet and backsheet in the side flap region 10. The diaper embodiment disclosed in FIGS. 1 and 2 further comprises elastic barrier flaps 12 having a proximal edge 13 and a distal edge 14 and elastic member 15 spacing the distal edge 14 away from the topsheet. These barrier flaps 12 form leakage barriers and are at their proximal edges 13 secured to the topsheet 2 close to the lateral edges of the absorbent core 4 either in the area of the side flaps 10 or above the absorbent core 4.

In another embodiment, the diaper may further comprise an elasticized waist feature in the form of elastic members extending in the transverse direction of the article in the waist portion thereof.

In a further embodiment, the diaper comprises belt portions attached to the rear portion of the diaper and intended to be fastened together around the waist of the wearer. Fastening means on the front part of the diaper are then attached to the outside of the belt to fasten together the diaper to the desired pantlike shape. An example of a belted diaper is shown in WO 01/00129.

However, it is understood that the diaper described above and shown in the drawing only represents one non-limiting example and that the present invention is not limited thereto, but can be used in any type of absorbent articles as defined above.

The absorbent article according to one embodiment of the present invention has a skin care composition applied on at least a portion thereof so as to be transferable to the skin of the wearer by normal contact, wearer motion, and/or body temperature. When transferred to the skin, the skin care composition provide desirable skin treating or protective benefits such as reduced red marking, erythema, diaper dermatitis, and skin irritation.

Several factors in combination lead to the development of diaper dermatitis or diaper rash. Wet skin results in that chafing and pressure more easily wear down the skin. A high moisture content also means that skin penetration by irritant substances can increase, and that bacteria and fungi can thrive. Occlusion of skin and breakdown of urea in the urine to ammonia results in an increase in the pH. The higher pH value leads to that enzymes (lipases and proteases) coming from the intestine, and from the microorganisms in the excrement, can break down the skin to a greater extent. A vicious cycle can easily develop in which various factors facilitate and intensify each other.

Dermatitis is best prevented by creating conditions, which counteract those factors which create and maintain the process of diaper dermatitis. It should therefore be endeavored to keep the skin as dry as possible, to air the skin often and to change wet diapers. Mechanical shearing forces should be minimized by choosing materials, which are as smooth and soft as possible, and wear between diaper and skin should be minimized. By supplying the skin with a softening and protective lotion or cream, it is further possible to strengthen the barrier against penetration of irritant substances and enzymes. In more serious cases of dermatitis, microorganisms may have infected the damaged skin, and treatment with more active medicines is required. Ointment with cortisone and various fungicidal and bactericidal agents may thus be used.

The skin care composition may be applied to any portion of the article that is in contact with the skin of the wearer during use either directly or through the pervious topsheet. Such portions include the topsheet 2 or part thereof, the elasticized side flaps 10, the barrier flaps, the belts in a belted diaper, the elastic members in the side flaps, barrier flaps, and/or waist portion. The skin care composition may also be applied to fibers contained in a nonwoven material and tow fibers in a tow material.

The skin care composition according to the invention is solid at 21° C. and comprises the following components:
a) 5% to 70% by weight of a component melting in the range from 25° C. to 37° C., chosen from the group of synthetic waxes, paraffins, fatty acid esters, polyhydroxy fatty acid esters, fatty alcohols, alkoxylated fatty acid esters, alkoxylated fatty alcohols and mixtures of these compounds;
b) 5% to 70% by weight of a component whose melting point is at least 5° C. higher than the melting point of component a), and component b) is chosen from the group of paraffins, polyhydroxy fatty acid esters, $C_{14}$-$C_{22}$ fatty alcohols, $C_{12}$-$C_{22}$ fatty acids, the alkoxylated derivatives of the fatty alcohols and fatty esters, and mixtures of these components; and
c) 5% to 25% by weight of a crystallization accelerator chosen from the group of partial glycerides, ethylene glycol diesters and polymeric waxes, with the proviso that the crystallization accelerator has a melting point in the range from 45° C. to 70° C., and that the compositions comprise less than 5% by weight of water.

Melting itself is defined as the transition of a substance from the solid to the liquid aggregate state by the input of thermal energy, where, as a consequence of an increase in kinetic energy of the particles, their oscillation amplitude becomes so great that the lattice structure collapses. The melting point is defined as the temperature at which the liquid and the solid phase of a substance are in thermodynamic equilibrium at a pressure of, normally, 1013 kPa. In actual fact, the term "melting point" is, however, used in practice mostly only for the transition point from the solid state to the liquid state, and not for the temperature, identical thereto, at which the transition in the reverse direction takes place. The amount of heat absorbed in this process is referred to as the heat of melting or the enthalpy of melting. Usually, the melting point increases with increasing pressure, although there are exceptions. For many pure substances, the melting points can be determined with great accuracy since here the temperature remains constant over a certain time interval during the introduction of heat. For amorphous, glass-like substances, there is no specific melting point since there are no crystal lattices here. Similar phenomena are observed in the melting behavior of fats, ointments, creams or suppository materials; in such cases, it is possible to use the solidification point, the so-called rise point and the dropping point for characterizations.

The action of this crystallization accelerator is to be understood as meaning it has a very sharp melting point which must be higher than the melting point of the liquid to semiliquid component a), but should be lower than the temperature at which the lotion is applied. The combination of component a), which melts at relatively low temperatures, with component b), which melts at higher temperatures, and the simultaneous addition of the crystallization accelerator c) gives lotions which, firstly, are still storage-stable even at high temperatures, and at the same time can be transferred from the article to the skin of the wearer while being worn.

Component a) can be chosen from a large number of compounds known to the person skilled in the art, it being preferable that the melting point is in the range from 25° C. to 37° C. Firstly, for this purpose it is possible to use certain paraffins, but also fatty acid esters and, in particular, fatty alcohols. Suitable paraffins are preferably semisolid paraffins, such as soft paraffin, preferably petrolatum. Suitable fatty alcohols are, for example, dodecanol or ricinol alcohol, to name one representative of the unsaturated fatty alcohols. Further suitable substances are chosen from the class of synthetic waxes, for example copolymers of polyethylene/maleic anhydride. For the purposes of the present invention, the use of glycerides is particularly suitable, preferably mixtures of partial glyceride and triglycerides, which have the desired melting point of from 25 to 37° C. Particular preference is given here to mixtures of glycerides of fatty acids having 8 to 18 carbon atoms.

Glycerides are mono-, di- and/or triesters of glycerol with fatty acids, namely, e.g., caproic acid, caprylic acid, 2-ethylhexanoic acid, capric acid, lauric acid, isotridecanoic acid, myristic acid, palmitic acid, palmoleic acid, stearic acid, isostearic acid, oleic acid, elaidic acid, petroselic acid, linoleic acid, linolenic acid, elaeostearic acid, arachidic acid, gadoleic acid, behenic acid, erucic acid, and technical-grade mixtures thereof. They conform to the formula (I),

in which R is a COR' radical, in which R' is a branched or unbranched, saturated or unsaturated alkyl radical having 6 to 22 carbon atoms, and/or independently thereof, is hydrogen. Typical examples are lauric acid monoglyceride, lauric acid diglyceride, coconut fatty acid monoglyceride, coconut fatty acid triglyceride, palmitic acid monoglyceride, palmitic acid triglyceride, stearic acid monoglyceride, stearic acid diglyceride, isostearic acid monoglyceride, isostearic acid diglyceride, oleic acid monoglyceride, oleic acid diglyceride, tallow fatty acid monoglyceride, tallow fatty acid diglyceride, behenic acid monoglyceride, behenic acid diglyceride, erucic acid monoglyceride, erucic acid diglyceride, and technical-grade mixtures thereof, which may also comprise small amounts of triglyceride as secondary components from the preparation process.

Suitable as component a) are, in particular, those mixtures of coconut partial glyceride and triglycerides sold under the trade name Novata®-B by SCA Hygiene Products AB. Novata®-B has a melting point (in accordance with DGF C-IV 3a) of from 33° C. to 36° C., and the acid number is 0.3 (in accordance with DGF C-V2). The saponification value is 225-240 in accordance with DGF C-V 3. The molecular weight is 710. A further suitable mixture for component a) is Novata®-299 (melting point 34° C.) also available from SCA Hygiene Products AB.

Component b) preferably has a melting point which is at least 5° C. higher than the melting point of component a) used in the composition in question. Particular preference is given here to those compounds of the group of $C_{14}$-$C_{22}$ fatty alcohols, $C_{12}$-$C_{22}$ fatty acids and alkoxylated derivatives thereof, and fatty alcohols and esters. However, hard paraffins having the desired melt properties are also suitable. In this case too, the mixtures of different glycerides or $C_8$-$C_{18}$ fatty acids, in particular, are suitable as component b) for the purposes of the present technical teaching. Especially suitable both for component a) and also b) are glycerol triesters and partial esters of coconut fatty acids. With these $C_8$-$C_{18}$ fatty acids, depending on the choice of chain lengths of the glycerides or of the degree of esterification, it is possible to create mixtures with varying melting points. Mixtures of lauric ($C_{14}$) and myristic ($C_{16}$) esters are preferably present.

The higher-melting component b) used is preferably Novata®-D, available from SCA Hygiene Products AB. Novata®-D is a mixture of triglycerides and partial glycerides of coconut fatty acids, but with a different melting range. Novata®-D has a melting point (in accordance with DGF C-IV 3a) of from 40° C. to 42° C., and the acid number is 0.3 (in accordance with DGF C-V2). The saponification value is 215-230 (in accordance with DGF C-V 3).

The use of the crystallization accelerator component c) is preferable in an embodiment of the present invention. This is a substance with a melting range which is, firstly, at least 45° C., and, secondly, is preferably as narrow as possible, e.g., does not extend over more than 4.5° C., preferably 2.5° C., and below.

Particularly suitable as component c) are selected glycerol partial esters with $C_{12}$-$C_{21}$ fatty acids, preferably glycerol monostearate, having a melting range in accordance with DGF C-IV 3a of 58° C.-60° C., or glycerol monolaurate, melting range according to DGF-C-IV 3a of 56° C.-60° C. Further suitable monoglycerides are glycerol monocaprate (melting point 53° C.) or glycerol myristate (melting point 70.5° C.).

If the crystallization accelerator c) according to an embodiment of the invention is used, lotions are obtained which can be applied to the article or to a material intended to be used therein, such as a topsheet nonwoven material, elastic members or the like without problem since their melting temperature is higher than that of the lower-melting component a), but is not so high that it reaches the application temperature of the lotion onto the article or material. The application temperature is preferably 60° C.-80° C., with the application temperature adapted depending on the crystallization accelerator used.

In selecting components a) to c), their melting points are, firstly of significance. In addition, it is to be taken into consideration that at least three different substances are present in the composition according to an embodiment of the invention. Component c) preferably has a melting point in the range from 30° C. to 35° C. It is particularly preferred if component c) has a melting point below the melting point of component b) and is preferably 5° C. to 10° C., in particular, 10° C. to 15° C., lower.

The compositions themselves preferably have a melting point in the range from 35° C. to 65° C., in particular from 35° C. to 50° C. and preferably 35° C. to 45° C. The melting behavior of the compositions influences the use, and it is therefore preferred for the compositions according to the invention to have two melting ranges, which are clearly separate from one another, as can preferably be ascertained by means of TLC measurements. The enthalpies of melting for the compositions are preferably 80 J/g to 160 J/g, in particular 90 J/g to 140 J/g and particularly preferably 100 J/g to 125 J/g. Furthermore, the co-use of liquid or semisolid compounds, as disclosed in the above-cited WO 96/16682, and also in WO 96/16681, is preferably excluded.

The compositions according to one embodiment of the invention are anhydrous, i.e., they comprise water in a total amount of 5% by weight, preferably 0.5% to 3% by weight and in particular 0.1% to 2.0% by weight. Accordingly, anhydrous components a) to c) are preferably to be chosen in order to avoid expensive drying steps during the preparation.

In preferred embodiments of the invention, component a) is present in amounts of 10% to 60% by weight, component b) is present in amounts of 10% to 60% by weight and component c) is present in amounts of 10% to 30% by weight.

In addition, further customary ingredients may also be present in the compositions according to one embodiment of the invention, e.g., silicone waxes or polysiloxanes, in amounts of from 1% to 6% by weight, preferably 1.5% to 5.5% by weight and, in particular, from 2% to 5% by weight. Polysiloxanes are known polymeric compounds, which contain the following structure as monomer units:

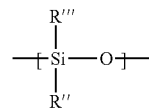

Here, R" and R''', independently of one another, are hydrogen or an alkyl, cycloalkyl, aryl, or alkenyl radicals. Siloxanes of this type preferably have viscosities at 37° C. in the range from 5 mPa-s to 5,000 mPa-s.

In addition, the compositions according to one embodiment of the invention may comprise skin-friendly or skincare substances, preferably in amounts of 0.1% to 10% by weight, in particular, 1% to 8% by weight and most preferably from 2% to 6% by weight.

Ingredients of this type may be, e.g., bisabolol, alantoin and panthenol. It is also possible to use vitamins, preferably vitamin E and vitamin precursors, and protein hydrolysates. Also suitable are plant extracts, preferably from camomile, aloe vera, lime blossom, horse chestnut, green tea, oak bark, stinging nettle, hops, burdock, horsetail, hawthorn, almond, spruce needle, almond wood, juniper, coconut, apricot, lemon, wheat, kiwi, melon, orange, grapefruit, sage, rosemary, birch, mallow, lady's smock, thyme, balm, restharrow, coltsfoot, althea, ginseng, and root ginger. In addition, however, other skincare substances may also be present. Those skincare substances include, in particular, chitosan, and zinc oxide or zinc ricinoleate.

A particularly preferred embodiment of the present invention comprises 50% to 60% by weight of a mixture of glycerol esters of coconut fatty acids having a melting point of from 30° C. to 33° C. as component a), 10% to 20% by weight of a linear, unsaturated fatty alcohol having a melting point of from 57° C. to 60° C. as component b), 15 to 20 parts of polyvinyl stearyl ether having a melting point of from 45° C. to 48° C. as component c), optionally 2% to 5% by weight of silicone wax, and optionally 5% to 10% by weight of a skincare substance, preferably of avocado oil.

The compositions in one embodiment are prepared in a manner customary per se, by mixing the individual liquid components, i.e., at elevated temperatures, preferably at 40°

C. to 80° C. and, in particular, at 50° C. to 70° C. A particular sequence during the mixing of the components is not necessary. The compositions are then cooled to room temperature (21° C.).

Since the skincare composition according to the invention solidifies rapidly it provides several advantages in the manufacturing process of absorbent articles, which takes place in a very high speed, several hundreds of articles per minute, or in the case of the production of nonwoven web materials, several hundreds of meters per minute. Due to the rapid solidification the composition, which is applied in a molten state, will solidify sufficiently before the article or material is folded or rolled up, so that smearing of the molten composition is avoided or at least reduced. The risk that the composition may penetrate through, e.g., the topsheet of the absorbent article, onto which it has been applied, and migrate into the absorbent core making this hydrophobic and less absorbent is further reduced or even avoided. More composition may further be applied on the article or material in the process since the solidification process is more rapid.

The skincare composition is preferably applied to, e.g., the topsheet material or any other material or component of an absorbent article, before said material or component is joined to the other components of the article. It may alternatively be applied to the absorbent article after the materials and components contained therein have been joined together. It may be applied by any useful technique known in the art, such as spraying, printing, slot-nozzle application, etc. It may be continuously applied or in discrete areas, in gradients or patterns.

The skincare composition may be applied in different amounts in different parts of the topsheet material. For example, the intended wetting region of the topsheet, which is the region located in the crotch region where the discharged body fluid will be received during use of the article, may contain no or a relatively smaller amount of skincare composition as compared to the regions of the topsheet material located outside the wetting region.

Two or more skincare compositions may further be applied in different regions of the article. Thus, e.g., a skin composition especially adapted to alleviate red markings caused by pressure may be used in the regions of the elastic members in the side flaps, barrier flaps and/or waist portion, while another skin composition especially adapted to alleviate diaper rash caused by skin irritation from urine and/or feces, may be applied on the topsheet material in those areas which will be wetted by body discharges. Accordingly, by using the skincare compositions disclosed herein there is provided a great freedom in choosing where and how the composition may be applied to the article or a material intended to be incorporated in an absorbent article.

EXAMPLES

The following compositions 1 and 2 according to the invention were prepared and their melting behavior was investigated. For this purpose, DSC measurements were carried out in each case. The heating/Cooling rates were 10K/min and −1 K/min respectively.

Composition 1:
a) 58% by weight of a mixture of partial glycerides and triglycerides of coconut fatty acids, melting point: 34° C.
b) 15% by weight of stearyl alcohol, melting point 56-58° C.
c) 20% by weight of polyvinyl stearyl ether, melting point 45° C.
d) 2% by weight of silicone wax The melting point of the composition was 49° C. The heat of melting was 112 J/g.

Composition 2:
a) 55% by weight of a mixture of partial glycerides and triglycerides of coconut fatty acids, melting point: 34° C.
b) 15% by weight of glycerol monolaurate, melting point 63° C.
c) 20% by weight of polyvinyl stearyl ether, melting point 45° C.
d) 5% by weight of silicone wax The melting point was 46° C. The heat of melting was 82 J/g.

The compositions described above can be applied to nonwovens without difficulty and are suitable for the preparation of nonwovens for hygiene products.

To determine the cooling characteristic of lotions according to various embodiments of the present invention, three lotions were prepared and heated to 70° C. Lotions 1 and 2 (corresponding to the above compositions 1 and 2) contain crystallization accelerators according to the invention. Lotion 3 (corresponding in part to composition 1 above) is free of crystallization accelerator.

The hot lotions were put (0.5 ml each) on a slanting glass plate (angle 35°). Then the distance was measured, until the drop comes to stop. For lotion 1 and 2, a distance of approximately 15 cm was measured. The lotion without component c) according to claim 1 required 21 cm to come to a stop.

The above embodiments are merely illustrative and are in no way intended to limit the present invention.

What is claimed is:

1. An absorbent article comprising:
a liquid permeable topsheet,
a liquid impermeable backsheet,
an absorbent body enclosed therebetween, and
a skincare composition applied on at least a portion of the absorbent article so as to be transferable to skin of a wearer, wherein the skincare composition is solid at 21° C. and comprises the following components:
a) 5% to 70% by weight of a component melting in the range from 25° C. to 37° C. selected from the group consisting of synthetic waxes, paraffins, fatty acid esters, polyhydroxy fatty acid esters, fatty alcohols, alkoxylated fatty acid esters, alkoxylated fatty alcohols, and mixtures thereof;
b) 5% to 70% by weight of a component whose melting point is at least 5° C. higher than the melting point of component a) wherein component b) is selected from the group consisting of paraffins, polyhydroxy fatty acid esters, C14-C22 fatty alcohols, C12-C22 fatty acids, alkoxylated fatty alcohols and fatty esters, and mixtures thereof; and
c) 5% to 25% by weight of a crystallization accelerator in the form of a polyvinyl stearyl ether, wherein the crystallization accelerator has a melting point in the range from 45 to 70° C.

2. The absorbent article of claim 1, wherein the skincare composition comprises less than 5% by weight of water.

3. The absorbent article of claim 1, wherein the absorbent article is a diaper, pant diaper, adult incontinence guard, sanitary napkin.

4. The absorbent article of claim 1, wherein component b) has a melting point of 40° C. to 60° C.

5. The absorbent article of claim 1, wherein component a) is a mixture of glycerides of fatty acids of 8 to 18 carbon atoms.

6. The absorbent article of claim 5, wherein the mixture of glycerides is a technical-grade mixture of partial glycerides and glycerides.

7. The absorbent article of claim 5, wherein the mixture of glycerides is a technical grade mixture of partial glycerides or glycerides.

8. The absorbent article of claim 1, wherein component b) is a mixture of glycerides of fatty acids of 8 to 18 carbon atoms.

9. The absorbent article of claim 8, wherein the mixture of glycerides is a technical-grade mixture of partial glycerides or glycerides.

10. The absorbent article of claim 8, wherein the mixture of glycerides is a technical-grade mixture of partial glycerides and glycerides.

11. The absorbent article of claim 1, wherein component b) is a mixture of lauric (C14) and myristic (C16) esters.

12. The absorbent article of claim 1, wherein component a) or component b) each comprise glycerol triesters or partial esters of coconut fatty acids.

13. The absorbent article of claim 1, wherein component a) and component b) each comprise glycerol triesters or partial esters of coconut fatty acids.

14. The absorbent article of claim 1, wherein the skincare composition comprises component a) in an amount of 10% to 60% by weight, component b) in an amount of 10 to 60% by weight, and component c) in an amount of 10% to 25% by weight.

15. The absorbent article of claim 1, wherein the skincare composition has a melting point of 35° C. to 65° C.

16. The absorbent article of claim 15, wherein the skincare composition has a melting point of 35° C. to 50° C.

17. The absorbent article of claim 16, wherein the skincare composition has a melting point of 35° C. to 45° C.

18. The absorbent article of claim 1, wherein the skincare composition further comprises a silicone wax in an amount of 1% to 6% by weight.

19. The absorbent article of claim 18, wherein the skincare composition comprises a silicone wax in an amount of 1.5% to 5.5% by weight.

20. The absorbent article of claim 19, wherein the skincare composition comprises a silicone wax in an amount of 2% to 5% by weight.

21. The absorbent article of claim 1, wherein the skincare composition further comprises a polysiloxane.

22. The absorbent article of claim 1, wherein the skincare composition further comprises a skin-friendly or skincare substance in an amount of 0.1% to 10% by weight.

23. The absorbent article of claim 22, wherein the skincare composition comprises a skin-friendly or skincare substance in an amount of 1% to 8% by weight.

24. The absorbent article of claim 23, wherein the skincare composition comprises a skin-friendly or skincare substance in an amount of 2% to 6% by weight.

25. The absorbent article of claim 22, wherein the skin-friendly or skincare substance is a vitamin or vitamin precursor, a protein hydrolysate, chamomile extract, aloe vera extract, lime blossom extract, horse chestnut extract, green tea extract, oak bark extract, stinging nettle extract, hops extract, burdock extract, horsetail extract, hawthorn extract, almond extract, spruce needle extract, almond wood extract, juniper extract, coconut extract, apricot extract, lemon extract, wheat extract, kiwi extract, melon extract, orange extract, grapefruit extract, sage extract, rosemary extract, birch extract, mallow extract, lady's smock extract, thyme extract, balm extract, restharrow extract, coltsfoot extract, althea extract, ginseng extract, root ginger extract, chitosan, zinc oxide, zinc ricinoleate, or avocado oil.

26. The absorbent article of claim 1, wherein the skincare composition comprises water in an amount of 0.5% to 3% by weight.

27. The absorbent article of claim 26, wherein the skincare composition comprises water in an amount of 0.5% to 2% by weight.

28. The absorbent article of claim 27, wherein the skincare composition comprises water in an amount of 0.5% to 1.5% by weight.

29. The absorbent article of claim 1, wherein the skincare composition comprises 50% to 60% by weight of a mixture of glycerol esters of coconut fatty acids having a melting point of 30° C. to 33° C. as component a), 10% to 20% by weight of a linear, unsaturated fatty alcohol having a melting point of from 57° C. to 60° C. as component b), 15% to 20% of polyvinyl stearyl ether having a melting point of from 45° C. to 48° C. as component c), optionally 2% to 5% by weight of silicone wax, and optionally 5% to 10% by weight of a skincare substance.

30. The absorbent article of claim 29, wherein the skincare substance is avocado oil.

31. The absorbent article of claim 1, wherein the skincare composition is applied on at least part of the liquid permeable topsheet.

32. The absorbent article of claim 31, wherein different amounts of skincare composition are applied in different zones of the liquid permeable topsheet.

33. The absorbent article of claim 32, wherein the wetting region of the topsheet contains no or a smaller amount of skincare composition as compared to surrounding regions of the topsheet.

34. The absorbent article of claim 1, wherein the skincare composition is applied on any portion of the absorbent article in contact with the skin of the wearer during use.

35. The absorbent article of claim 34, wherein the portion of the absorbent article in contact with the skin of the wearer during use is an elastic member, a belt, or fibers.

36. The absorbent article of claim 1, wherein at least two different skincare compositions are applied in different regions of the article.

37. The absorbent article of claim 1, wherein the skincare composition comprises
    58% by weight of a mixture of partial glycerides and triglyerides of coconut fatty acids;
    15% by weight of stearyl alcohol;
    20% by weight of polyvinyl stearyl ether; and
    2% by weight of silicone wax.

38. The absorbent article of claim 1, wherein the skincare composition comprises
    55% by weight of a mixture of partial glycerides and triglycerides of coconut fatty acids;
    15% by weight of glycerol monolaurate;
    20% by weight of polyvinyl stearyl ether; and
    5% by weight of silicone wax.

39. The absorbent article of claim 1, wherein the liquid permeable topsheet comprises nonwoven material.

40. The absorbent article of claim 39, wherein the nonwoven material is spunbonded, meltblown, carded, hydroentangled, or wetlaid material.

41. The absorbent article of claim 39, wherein the nonwoven material is a natural or manmade fiber or a mixture thereof.

42. The absorbent article of claim 41, wherein the natural or manmade fiber or mixture thereof is woodpulp fiber, cotton fiber, polyester, polyethylene, polypropylene, viscose, or a mixture thereof.

43. The absorbent article of claim 1, wherein the liquid permeable topsheet comprises tow fibers, porous foam, or apertured plastic film.

44. The absorbent article of claim 1, wherein the liquid-impermeable backsheet comprises a thin plastic film, a nonwoven material coated with a liquid-impervious material, a hydrophobic nonwoven material, or a laminate of plastic film and nonwoven material.

45. The absorbent article of claim 44, wherein the thin plastic film is polyethylene or polypropylene film.

46. The absorbent article of claim 1, wherein the liquid permeable topsheet and liquid impermeable backsheet are connected to each other by gluing, heat welding, or ultrasonic welding.

47. The absorbent article of claim 1, wherein the liquid permeable topsheet or liquid impermeable backsheet are attached to the absorbent body.

48. The absorbent article of claim 1, wherein the absorbent body is cellulosic fluff pulp, tissue layers, superabsorbent polymer, absorbent foam material, absorbent nonwoven materials, or combinations thereof.

49. A method of making an absorbent article with a skincare composition, the absorbent article comprising:
   a liquid permeable topsheet;
   a liquid impermeable backsheet; and
   an absorbent body enclosed therebetween,
   the method comprising applying a skincare composition on at least a portion of the absorbent article so as to be transferable to skin of a wearer of the absorbent article, wherein the skincare composition is solid at 21° C. and comprises the following components:
   a) 5% to 70% by weight of a component melting in the range from 25° C. to 37° C. selected from the group consisting of synthetic waxes, paraffins, fatty acid esters, polyhydroxy fatty acid esters, fatty alcohols, alkoxylated fatty acid esters, alkoxylated fatty alcohols, and mixtures thereof;
   b) 5% to 70% by weight of a component whose melting point is at least 5° C. higher than the melting point of component a) wherein component b) is selected from the group consisting of paraffins, polyhydroxy fatty acid esters, C14-C22 fatty alcohols, C12-C22 fatty acids, alkoxylated fatty alcohols and fatty esters, and mixtures thereof; and
   c) 5% to 25% by weight of a crystallization accelerator in the form of a polyvinyl stearyl ether, wherein the crystallization accelerator has a melting point in the range from 45 to 70° C.

50. The method of claim 49, wherein the skincare composition comprises less than 5% by weight of water.

51. The method of claim 49, wherein the skincare composition is prepared by mixing components a) to c) together at a temperature of between 40° C. and 80° C., followed by cooling to room temperature.

52. The method of claim 51, wherein components a) to c) are mixed together at a temperature of between 50° C. and 70° C.

53. The method of claim 49, wherein the skincare composition is applied to a topsheet material of the absorbent article.

54. The method of claim 49, wherein the skincare composition is applied to the absorbent article or material to be incorporated into an absorbent article by spraying, printing, or slot-nozzle application.

55. The method of claim 49, wherein the skincare composition is applied to the absorbent article or material to be incorporated into an absorbent article in a continuous or discrete application.

56. The method of claim 49, wherein the skincare composition is applied to the absorbent article or material to be incorporated into an absorbent article in a gradient or pattern.

57. The method of claim 49, wherein a wetting region of a topsheet of the absorbent article contains no or a smaller amount of skincare composition as compared to surrounding regions of the topsheet.

58. The method of claim 49, wherein the skincare composition is applied to a portion of the absorbent article in contact with the skin of the wearer during use.

59. The method of claim 58, wherein the skincare composition is applied to an elastic member, a belt, or fibers.

60. The method of claim 49, wherein the skincare composition is applied to a material to be incorporated into an absorbent article before the material is joined to other components of the absorbent article.

61. The method of claim 49, wherein the skincare composition is applied to the absorbent article after materials and components of the absorbent article are joined together.

62. The method of claim 49, wherein at least two different skincare compositions are applied in different regions of the absorbent article.

* * * * *